United States Patent [19]

Gieles et al.

[11] 4,057,063
[45] Nov. 8, 1977

[54] DEVICE FOR STERILIZATION BY TRANSUTERINE TUBE COAGULATION

[75] Inventors: Antonius Cornelis Maria Gieles; Gerardus Henricus Johannus Somers, both of Eindhoven, Netherlands

[73] Assignee: U.S. Philips Corporation, New York, N.Y.

[21] Appl. No.: 661,947

[22] Filed: Feb. 27, 1976

[30] Foreign Application Priority Data

Nov. 4, 1975 Netherlands .......................... 7504321

[51] Int. Cl.² .................... A61B 17/36; A61N 3/04
[52] U.S. Cl. ................................ 128/303.17; 128/408
[58] Field of Search ................. 128/303.17, 303.13, 128/303.14, 303.15, 303.16, 303.18, 408, 419 R, 419 D

[56] References Cited

U.S. PATENT DOCUMENTS

| 2,102,270 | 12/1937 | Hyams | 128/303.17 |
| 3,163,165 | 12/1964 | Isikawa | 128/303.17 |
| 3,634,652 | 1/1972 | Shimizu et al. | 128/303.18 X |
| 3,840,016 | 10/1974 | Lindemann | 128/303.17 |
| 3,858,586 | 1/1975 | Lessen | 128/303.17 |
| 3,862,636 | 1/1975 | Bell et al. | 128/419 D |
| 3,875,945 | 4/1975 | Friedman | 128/303.17 |
| 3,920,021 | 11/1975 | Hiltebrandt | 128/303.17 |

FOREIGN PATENT DOCUMENTS

| 1,347,865 | 1/1964 | France | 128/303.14 |
| 855,459 | 11/1960 | United Kingdom | 128/303.17 |

OTHER PUBLICATIONS

Decker et al., "An electrocautery Instrument . . . for Sterilization," Instrument Society of America Reprint, May, 1973, pp. 4–10.

Primary Examiner—Robert W. Michell
Assistant Examiner—Lee S. Cohen
Attorney, Agent, or Firm—Frank R. Trifari

[57] ABSTRACT

A device for sterilizing human females by transuterine fallopian tube coagulation wherein the substantial increase in impedance of the tissues during coagulation is used to signal for termination of treatment.

6 Claims, 4 Drawing Figures

DEVICE FOR STERILIZATION BY TRANSUTERINE TUBE COAGULATION

The invention relates to a device for sterilizing human females by transuterine tube coagulation, comprising a high frequency generator and a probe which is connected thereto and which comprises an active electrode.

It is possible to sterilize human females, in the so-called transuterine tube coagulation method, by sealing the lumen of the tubes leading to the uterus by electric coagulation of the tissue. According to a known method, (see, for example, an article by H. J. Lindemann in "Geburtsh. und Frauenheilk.", No. 33 (1973) pages 709–715, published by Georg Thieme Verlag, Stuttgart), a coagulation probe is moved to the tube under visual control by means of an hysteroscope. This method is substantially less disturbing to the patient than an operation through the abdominal wall, but it still requires narcosis or a local anaesthetic.

The invention has for its object to provide a device for transuterine tube coagulation whereby the sterilization can be very quickly and accurately performed without utilizing a hysteroscope and hence without narcosis. To this end, the device according to the invention is characterized in that the probe is formed by a flexible catheter comprising on one end a metal portion which forms the active electrode and which is electrically connected to a connection which is provided near the other end of the catheter, the device furthermore comprising indicating means for providing information as regards the variation of the current and the voltage delivered by the generator.

The catheter can be positioned under X-ray control, after which the metal electrode closes the opening of one of the tubes leading to the uterus like a cork closes a bottle. This can be checked by injecting an X-ray contrast liquid via the catheter. When the electrode has been properly positioned, only the tube gives X-ray contrast and the uterus itself does not. The current and voltage values give an indication which enable the coagulation process to be followed and terminated at the most suitable instant without visual checking. The indicating means preferably comprise a first lamp which lights up when the voltage on the electrode increases beyond a given value, and a second lamp which extinguishes when the current applied to the electrode decreases below a given value. In order to accurately follow the coagulation process, it may furthermore be important to monitor the variation of the resistance of the tissue and the power delivered to the tissue. These quantities can be calculated from the measured current and voltage by means of suitable calculating members.

In order to check the circuit formed by the generator, the electrode and the tissue for an open circuit and possibly dangerous defects after the positioning of the electrode, just prior to the beginning of the treatment, there is preferably provided a switch whereby the catheter connection can be connected to the generator via a circuit which limits the current intensity supplied by the generator to a value which is substantially lower than the current intensity required for tissue coagulation, while a measuring instrument is provided for measuring at the same time the voltage on the connection.

The invention will be described in detail hereinafter with reference to the drawing.

FIG. 1 diagrammatically illustrates the principle of a device according to the invention, FIG. 2 shows the variation of the current and the voltage during sterilization.

Figures 1, 2:
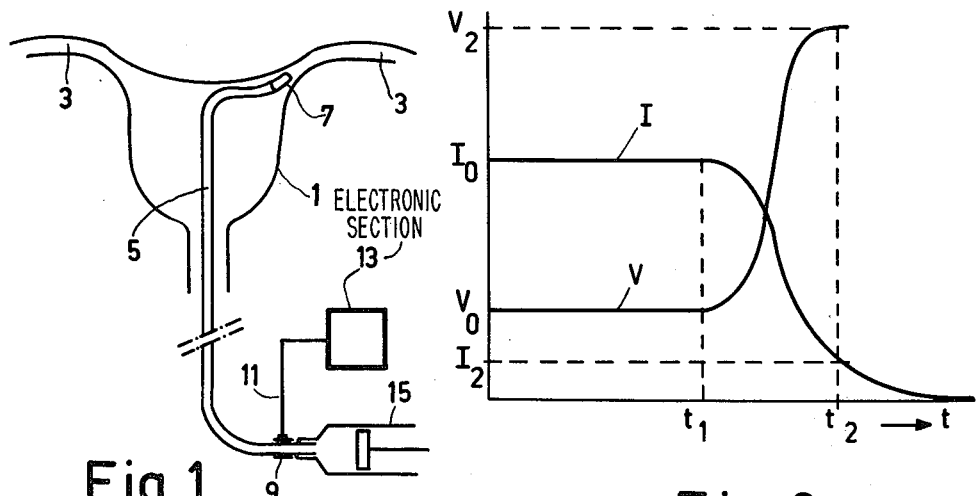

FIG. 1 diagrammatically shows a uterus 1 and tubes 3 opening therein. A thin flexible catheter 5 has been introduced to the uterus. An end portion of this catheter has been bent to be approximately S-shaped, with result that the end of the catheter automatically searches the opening of one of the fallopian tubes 3. This end portion is partly made of metal in order to form an active electrode 7 which is connected, via a conductor (not shown) extending in the wall of the catheter 5 to a metal connection portion 9 near the other end of the catheter, which in its turn is connected, via a conductor 11, to the electronic section 13 of the device which will be described in detail hereinafter with reference to FIG. 3. The internal cavity of the catheter is connected to a known pumping device 15 for injecting X-ray contrast liquid. When the catheter 5, inserted under X-ray control, is slid slightly further than the position shown, the electrode 7 closes off the tube 3 like a cork closes a bottle. When contrast liquid is then injected by means of the pumping device 15, only the tube 3 will be clearly visible in the X-ray image. When closure by the electrode 7 is complete, contrast liquid will also penetrate into the uterus 1; this can be clearly observed in the X-ray image.

After the X-ray check has revealed that the electrode 7 occupies the correct position, the electronic section 13 is activated. This section delivers a series of current surges of high frequency, for example 2 MHz as is commonly done for tissue coagulation (see, for example, U.S. Pat. No. 3,675,655. Normal tissue contains a larger quantity of moisture and hence has a low specific resistance. During and after the coagulation process by means of high frequency energy, this moisture evaporates and the tissue is dessicated. If the application of high frequency energy is continued, the tissue carbonizes. During the dessication phase the specific resistance of the tissue substantially increases; this becomes manifest in an increase of the voltage and a decrease of the current. This is shown in FIG. 2, wherein the current I and the voltage V are plotted as a function of the time. The dessication commences at the instant $t_1$ and the carbonizing commences approximately at the instant $t_2$ at which the treatment is terminated.

Figure 3:
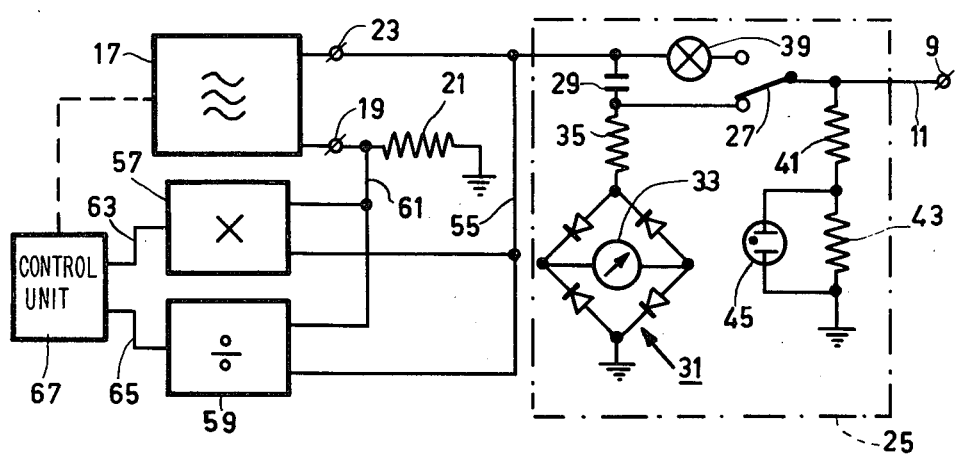
FIG. 3 shows a block diagram of the device according to the invention.

The object of transuterine tube coagulation is to damage the tissue of the tubes 3 such that scar tissue is produced which effectively seals the opening of the tubes. It has been found that an optimum effect is achieved if the coagulation is terminated approximately at the indicated instant $t_2$, i.e. during or shortly after the end of the desication phase. As appears from FIG. 2, this instant is characterized by a voltage $V_2$ and a current $I_2$. It has been found that proper control of the process can be achieved by measuring the r.m.s. values of current and voltage, and particularly by indicating the reaching of the values $I_2$ and $V_2$. To this end, the electronic section 13 can be constructed as shown by FIG. 3 in the form of a block diagram.

One output 19 of a known high frequency generator 17 (see, for example, said U.S. Pat. No. 3,675,655) is earthed via a resistor 21, while the other output 23 is connected to the catheter connection 9 via a control unit 25 and the conductor 11.

The control unit 25 comprises a switch 27 which, in the position shown, connects the generator output 23 to the connection 9 via a voltage divider formed by a capacitor 29 and a resistor 35. This voltage divider is chosed such that the generator current remains limited to a value which lies substantially below the current required for tissue coagulation. The voltage on the connection 9 (which is also substantially below the generator voltage) is then a measure of the resistance of the series circuit formed by the construction 9, the conductor in the catheter 5, the active electrode 7, the tissue of the patient and an earthed neutral electrode (not shown). If this series circuit does not include poor contacts, its resistance amounts to approximately 150 Ω. A poor contact in the circuit can be caused, for example, by the neutral electrode inadequately contacting the skin of the patient. A poor contact becomes manifest in a substantially high resistance and may be hazardous to the patient.

The voltage on the connection 9 is measured by a rectifier bridge 31 with a measuring instrument 33. The bridge 31 is connected, via the said resistor 35, to the capacitor 29. When the desired measurement reveals that everything is in order, the switch 27 can be switched over, after which the output 23 of the generator 19 is connected to the connection 9 via an incandescent lamp 39. In comparison with the said series circuit, the incandescent lamp 39 has a low resistance, so that the full generator current $I_0$ (see FIG. 2) can flow. The incandescent lamp 39 extinguishes substantially completely when the current decreases substantially, i.e. approximately at the instant $t_2$.

Figure 4:
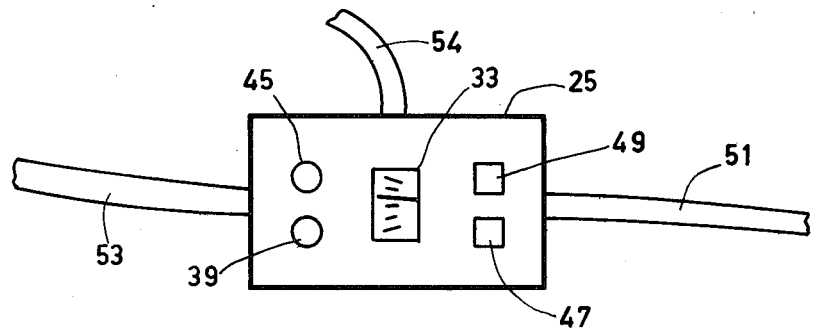
FIG. 4 is a front view of a control unit for this device.

The connection 9 also has connected thereto, via a voltage divider formed by two resistors 41, 43, a gas discharge lamp 45. The gas discharge lamp 45 lights up when the voltage on the connection 9 reaches a given value, for example $V_2$. The output voltage at which the gas discharge lamp lights up depends on the value of the resistor 41 and can be varied, if desired, by making this resistor variable. Due to these provisions, the reaching of the instant $t_2$ can be readily observed by the physician on the basis of the extinguishing of the lamp (39) and the approximately simultaneously lighting up of the lamp 45. The control unit 25 is preferably constructed as a case which can be easily held in the hand and which comprises a front panel whereon the lamps (39) and 45, the meter 33, a control knob 47 for the switch 27 and a control knob 49 for an on/off switch (not shown in FIG. 3) are provided (see FIG. 4). A first cable 51 connects the control unit 25 to the generator 17; a second cable 53 leads to the catheter connection 9, and a third cable 54 leads to the neutral electrode.

Besides by means of the control unit 25, which keeps the physician directly informed as regards the progress of the coagulation process, current and voltage measurements can also be effected at the area of the generator 17. The results of these measurements can be used for obtaining further information as regards the progress of the process or for controlling the generator. To this end, the output 23 of the generator 17, carrying the voltage V, is connected, via a conductor 55, to a multiplier 57 and a divider 59 which are known per se and which are not elaborated herein. The output 19, carrying a voltage proportional to the current I due to the resistor 21, is also connected, via a conductor 61, to the multiplier 57 and the divider 59.

The multiplier 57 calculates the product V.I. which corresponds to the r.m.s. value of the power P delivered by the generator 17. The divider 59 calculates the quotient V/I which corresponds to the load resistance R of the generator 17 which is mainly determined by the specific resistance of the treated tissue and which thus provides direct information as regards the progress of the coagulation process. Voltages which are proportional to P and R are applied, via conductors 63 and 65, respectively, to a known control unit 67 which controls the generator 17. If desired, the values of P and R can also be displayed in known manner (not shown).

What is claimed is:

1. A device for sterilizing human females by transuterine tube coagulation, comprising:
   means for generating a high frequency voltage;
   flexible catheter probe means having an electrode end portion dimensioned to completely contact the wall area of a fallopian tube for transuterine placement of said electrode end portion thereof into said fallopian tube of a human female, means including said probe means for coupling said voltage from said means for generating to said electrode end portion, thereby delivering high frequency voltage from said generating means to said fallopian tube;
   means for making a common ground connection between said generating means and the human female;
   means responsive to the impedance of the tissues adjacent said electrode end portion for signalling when the substantial increase therein occurs indicative of the substantial completion of the dessication phase of the destruction of said tissues; and
   means for interrupting delivery of high frequency voltage to said electrode end portion in response to said signalling thereupon.

2. A device as defined in claim 1 wherein said means for signalling comprises an incandescent lamp for indicating said substantial increase, said lamp being connected in series between said generating means and said electrode end portion, said lamp substantially extinguishes upon the reduction of current therethrough resulting from said substantial impedance increase.

3. A device as defined in claim 2 wherein at the side of said incandescent lamp connected to said electrode end portion, a voltage increase occurs as a result of said substantial impedance increase, said means for signalling further comprising a gas discharge lamp connected to said electrode end portion which energizes upon said voltage increase.

4. A device as defined in claim 1 wherein said means for signalling comprises an impedance in series between said generating means and said electrode end portion so that at the side thereof adjacent said electrode end portion a voltage increase occurs as a result of said substantial tissues impedance increase, and a gas discharge lamp connected to said electrode end portion which energizes upon said voltage increase.

5. A device as defined in claim 4 wherein said series impedance is an incandescent lamp which substantially extinguishes upon the reduction of current therethrough resulting from said substantial impedance increase.

6. A device as defined in claim 1, and further comprising means for applying to said electrode end portion a test voltage which is too low to cause coagulation, and means for measuring the voltage and current supplied to said electrode end portion for determining the initial value of said tissue impedance.

* * * * *